United States Patent [19]

Holtkamp, Sr.

[11] Patent Number: Plant 7,704

[45] Date of Patent: Nov. 5, 1991

[54] AFRICAN VIOLET PLANT NAMED LITTLE BLACKFOOT GIRL

[76] Inventor: Reinhold Holtkamp, Sr.,
Blumenstrasse 28, D 4242
Rees-Haffen, Fed. Rep. of Germany

[21] Appl. No.: 565,315

[22] Filed: Aug. 10, 1990

[51] Int. Cl.[5] ..... A01H 5/00
[52] U.S. Cl. ..... Plt./69
[58] Field of Search ..... Plt./69

*Primary Examiner*—James R. Feyrer
*Attorney, Agent, or Firm*—Foley & Lardner

[57] ABSTRACT

A new and distinct cultivar of African violet named Little Blackfoot Girl characterized by its mid-size growth habit (13–15 cm in diameter); purplish red, single violet-shaped flowers; strong stems which curve toward the center to form a compact bouquet above the leaves; profuse flowering; an abundance of blooms at one time, and continuous flowering; dark green, spear-shaped leaves; flowering 10–11 weeks after planting of unrooted shoot, and by its long lasting and non-dropping flowers.

1 Drawing Sheet

The present invention comprises a new and distinct cultivar of African violet plant, botanically known as *Saintpaulia ionantha,* and hereinafter referred to by the cultivar name Little Blackfoot Girl.

The new cultivar was referred to during the breeding and selection process by the designation 560/1 Medi red and is a product of a planned breeding program. The new cultivar was originated from a cross made by me in the controlled breeding program in Haffen, Federal Republic of Germany. The female, or seed parent was a cultivar designated 4 bl. The male, or pollen parent was a cultivar designated 0680 rot.

Little Blackfoot Girl was discovered and selected by me as a flowering plant within the progeny of the stated cross in a controlled environment in Haffen, West Germany. Asexual reproduction of the new cultivar by leaf cuttings, as performed by me at Haffen, West Germany, has demonstrated that the combination of characteristics as herein disclosed for the new cultivar are firmly fixed and retained through successive generations of asexual reproduction.

Little Blackfoot Girl has not been observed under all possible environmental conditions. The phenotype may vary significantly with variations in environment such as temperature, light intensity and day length. The following observations, measurements and values describe the new cultivar as grown in a 5.5 cm pot in Haffen, West Germany and Nashville, Tenn. under greenhouse conditions which closely approximate those generally used in commercial practice.

The following traits have been repeatedly observed and are determined to be basic characteristics of Little Blackfoot Girl, which in combination distinguish this African violet as a new and distinct cultivar:

(1) A single crown will not grow larger than 13–15 cm.

(2) Single violet-shaped, purplish-red flowers.

(3) Strong wirelike and upright flower stems curving toward the center.

(4) First flash of flowers form a tight bouquet above the leaves.

(5) There is always an abundance of flowers in bloom, and the flowering is continuous.

(6) Each plant carries 7–10 and more upright flower stems each of which carries 5–7 and more flowers.

(7) Long lasting, non-dropping flowers.

(8) Plant saleable 10 to 11 weeks after planting of unrooted shoot.

(9) Seed capsules push slightly through.

(10) Dark green, spear-shaped leaves are 3–4 cm in size.

(11) After maturity the flowers dry off, and remain on the peduncle.

The accompanying color photographic drawing shows a typical specimen plant of the new cultivar grown in a 5.5 cm pot. The colors appearing in the photograph are as true as possible with color illustrations of this type.

In the following description, color references are made to the Royal Horticultural Society Colour Chart (R.H.S.), except where general colors of ordinary significance are referred to. Color values were taken under natural sunlight conditions at approximately 12 a.m. in Nashville, Tenn.

Botanical classification: *Saintpaulia ionantha,* Ramat., c.v. Little Blackfoot Girl.

Parentage:

*Male parent.*—0680 rot.

*Female parent.*—4 bl.

Propagation: The new cultivar holds its distinguishing characteristics through successive propagations by leaf cuttings.

Plant: From 6 cm to 8 cm tall when grown in pots, and approximately 12–14 cm in diameter when fully grown.

Leaves:

*General form.*—Spear-shaped.

*Diameter.*—27–32 mm wide and 35–40 mm long.

*Texture.*—Leatherlike.

*Aspect.*—Hairy, slightly shiny, slightly serrated.

*Veins.*—Upperside: visible; underside: well pronounced, light green to pinkish green, shiny.

*Color (upperside).*—Yellow-Green Group 147 A and darker.

*Color (underside).*—Greyed-Purple 186 A and darker.

*Petiole.*—Strong, green with purplish red touch, hairy.

Flowers:

*Buds.*—Size: 6–8 mm just before opening. Shape: Bell-shaped. Color: Purplish red.

*Sepals.*—Five (5). Color: Purplish brown.

*Calyx.*—Shape: Funnel-shaped. Aspect: Spear-shaped, hairy.

*Peduncle.*—Character: Strong upright, hairy. Color: Green with purplish red touch.

Individual flowers:

*Size.*—25–28 mm.

*Shape.*—Single violet-shaped (3 large, 2 small petals).

*Color (upperside).*—Between Purple Group 77 A and Red-Purple Group 71 A. Under cooler temperatures and more intensive lighting, the purplish red tends to intensify.

*Color (underside).*—Purple-Violet Group 80 A to B.

*Borne.*—Each flower stem carries 5–7 and more flowers on strong, upright peduncles that are free standing above the leaves, thereby forming a compact bouquet.

*Flowering habit.*—Flowers 10–11 weeks after planting an unrooted plantlet.

Reproductive organs:

*Stamens.*—Two (2). Anthers: 2 composed of 4 anther cells, seed capsule pushes slightly through.

*Filaments.*—Yellowish green with purplish red on edges, 3–4 mm long.

*Styles.*—5–7 mm long, purplish red, base of ovary light green and hairy.

Roots: Normally developed, white when young, turning slightly brownish when older.

Disease resistance: Up to date, Little Blackfoot Girl has shown very good resistance to all major violet diseases.

General observations: Little Blackfoot Girl is a mid-size violet, a size between a regular violet (grown in a 10 cm pot) and a superminiature (grown in a 4 cm pot). Little Blackfoot Girl is designed to be grown in a 5.5 to 6 cm pot and will not grow larger than 13–15 cm. Each of the 7–10 and more strong flower stems carries 5–7 and more single, purplish red flowers. Occasionally, an additional larger petal and 1–2 very small petals over the anthers may develop. The flowers are long-lasting and non-dropping. A nice bouquet of flowers free standing above the dark green, spear-shaped leaves develops approximately 10–11 weeks after planting an unrooted plantlet. Little Blackfoot Girl has the characteristics of an abundance of blooms at one time, and continuous flowering.

I claim:

1. A new and distinct cultivar of African violet named Little Blackfoot Girl, as described and illustrated, and particularly characterized by its mid-size growth habit (13–15 cm in diameter); purplish red, single violet-shaped flowers; strong stems which curve toward the center to form a compact bouquet above the leaves; profuse flowering; an abundance of blooms at one time, and continuous flowering; dark green, spear-shaped leaves; flowering 10–11 weeks after planting of unrooted shoot, and by its long lasting and non-dropping flowers.

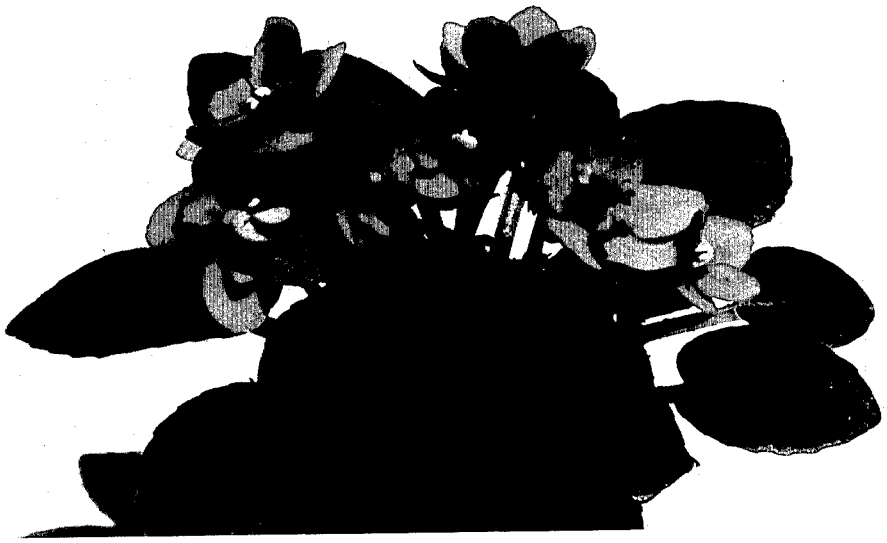

* * * * *